(12) United States Patent
Oh et al.

(10) Patent No.: US 11,565,008 B2
(45) Date of Patent: Jan. 31, 2023

(54) CLEANER FOR BED

(71) Applicant: LG ELECTRONICS INC., Seoul (KR)

(72) Inventors: Minkyu Oh, Seoul (KR); Yanghwan No, Seoul (KR); Keunho Ju, Seoul (KR); Hyunshin Kee, Seoul (KR)

(73) Assignee: LG ELECTRONICS INC., Seoul (KR)

(*) Notice: Subject to any disclaimer, the term of this patent is extended or adjusted under 35 U.S.C. 154(b) by 523 days.

(21) Appl. No.: 16/679,849

(22) Filed: Nov. 11, 2019

(65) Prior Publication Data
US 2020/0171183 A1 Jun. 4, 2020

(30) Foreign Application Priority Data
Dec. 4, 2018 (KR) .................. 10-2018-0154350

(51) Int. Cl.
*A61L 2/10* (2006.01)

(52) U.S. Cl.
CPC ............. *A61L 2/10* (2013.01); *A61L 2202/14* (2013.01); *A61L 2202/26* (2013.01)

(58) Field of Classification Search
CPC ............................. A61L 2202/26; A47L 7/008
See application file for complete search history.

(56) References Cited

U.S. PATENT DOCUMENTS

2005/0055792 A1    3/2005  Kisela et al.
2011/0095206 A1*   4/2011  Noto .................. A61L 2/10
                                                      250/492.1

FOREIGN PATENT DOCUMENTS

| CN | 204861855 U | 12/2015 |
| CN | 105747681 A | 7/2016 |
| CN | 106075493 A | 11/2016 |
| CN | 106175247 A | 12/2016 |
| CN | 207136647 U | 3/2018 |
| CN | 108354755 A | 8/2018 |
| JP | 2010194122 A | 9/2010 |
| KR | 20090111632 A | 10/2009 |
| KR | 1020170050473 A | 5/2017 |
| KR | 10-2017-0135024 A | 12/2017 |

OTHER PUBLICATIONS

Machine translation: CN 108354755, Zhou, S. (Year: 2018).*

* cited by examiner

*Primary Examiner* — Natasha N Campbell
(74) *Attorney, Agent, or Firm* — Dentons US LLP

(57) ABSTRACT

A cleaner for a bed includes a cleaning body provided to be movable forward or backward with respect to a surface of a mattress of the bed to suck foreign matter from the mattress, and thus the mattress may be easily cleaned.

19 Claims, 17 Drawing Sheets

CLEANER FOR BED

CROSS-REFERENCE TO RELATED APPLICATIONS

This application claims the benefit of the Korean Patent Application No. 10-2018-0154350 filed on Dec. 4, 2018, which is hereby incorporated by reference as if fully set forth herein.

BACKGROUND

Field of the Invention

The present disclosure relates to a cleaner for a bed.

Discussion of the Related Art

Recently, it is common for each home to have a bed. In order to ensure a comfortable bed time, interest in hygienic care of beds has increased in line with an increase in functional requirements of beds.

In particular, a mattress of a bed may be easily contaminated due to user's sweat or dust at home. In addition, harmful organisms such as bacteria or mites or germs that may inhabit the mattress due to the contamination may threaten user's health.

Therefore, users use a professional bed care company to clean or sterilize the mattress of the bed in many cases. This, however, incurs high cost.

Korean Patent Laid-open Publication No. (Pubication Date): 10-2017-0135024 (Dec. 8, 2017) discloses a device for sterilizing a bed.

Sterilization is performed using steam. However, this leads to a possibility of damage to the bed mattress.

In addition, steam sprayed from a sterilizer must be high in order to act on a large area of a mattress, and to this end, a steam body extending in a longitudinal direction must be provided, causing a problem in that a size of the sterilizer is too large.

SUMMARY

An aspect of the present disclosure is directed to providing a cleaner for a bed, which may be positioned adjacent to a surface of a mattress of the bed, thus increasing cleaning efficiency of the mattress and reducing a volume of cleaner.

Another aspect of the present disclosure is directed to providing a cleaner for a bed, which allows a user to use the bed even with the cleaner installed therein, thus eliminating the necessity for the cleaner to be attached to or detached from the bed each time the cleaner is used.

Another aspect of the present disclosure is directed to providing a cleaner for a bed, which may be provided to be movable up and down with reference to a lengthwise direction of a mattress of the bed.

Another aspect of the present disclosure is directed to providing a cleaner for a bed, capable of sucking dust present in a mattress through a dust suction port formed on a bottom surface or an upper surface of the cleaner.

Another aspect of the present disclosure is directed to providing a cleaner for a bed, capable of removing harmful germs (or bacteria) by disposing an irradiation source irradiating ultraviolet rays to the cleaner.

Another aspect of the present disclosure is directed to providing a cleaner for a bed, which can be adjusted in height according to a sensing result of a sensor which senses an obstacle or a sensor which senses a distance to a surface of a mattress provided therein.

Another aspect of the present disclosure is directed to providing a cleaner for a bed, in which a main body is provided on an upper surface or a lower surface of a mattress to easily remove dust or the like present on the surface of the mattress.

Another aspect of the present disclosure is directed to providing a cleaner for a bed, which includes a dust flow path guiding movement of dust sucked into the cleaner and the dust flow path includes a variable flow path varied in length or shape, thereby allowing dust to be easily sucked and moved even while the cleaner is moving.

Another aspect of the present disclosure is directed to providing a cleaner for a bed, which may be smoothly moved by a transfer guide device guiding movement of the cleaner.

To achieve these and other advantages and in accordance with the purpose of the disclosure, as embodied and broadly described herein, there is provided a cleaner for a bed, including a cleaning body provided to be movable forward or backward with respect to a surface of a mattress, the cleaning body having a suction portion for sucking foreign matter from the mattress, whereby the mattress may be easily cleaned.

The cleaner may further include a cleaning motor configured to communicate with the cleaning body and to generate a suction force and a dust box connected to the cleaning motor and configured to store the foreign matter sucked through the suction portion, whereby the mattress may be easily vacuum-cleaned.

The cleaner may include a transfer motor to facilitate movement of the cleaning body.

The cleaning body may include a first part extending in a horizontal direction with respect to an upper surface of the mattress and a second part extending in a longitudinal direction from both sides of the first part and facing side surfaces of the mattress, whereby the cleaning body may be easily disposed to be adjacent to the mattress.

The first part may be provided to be movable upward or downward, making it easy to adjust a distance between the cleaning body and an outer surface of the mattress.

The cleaner may further include: a vertical motor provided at the cleaning body and configured to provide a driving force for moving the first part upward or downward, and a slider connected to the vertical motor and the first part.

The cleaner may further include: a bottom sensor provided at a bottom portion of the first part and configured to sense a distance between the mattress and the first part, wherein the vertical motor is driven based on a result sensed by the bottom sensor.

The cleaner may further include: a front sensor provided on a front surface portion of the first part and configured to sense whether an object is present at the mattress, wherein the transfer motor is driven based on a result sensed by the front sensor.

The suction portion may be provided at a bottom portion of the first part.

An ultraviolet light source for sterilizing the mattress may be provided at a bottom portion of the first part.

The cleaner may further include: a dust flow path connecting the cleaning body and the dust box.

The dust flow path may include a variable flow path changed in a shape when the cleaning body moves forward or backward.

The cleaner may further include: a pinion gear connected to the transfer motor; and a rack interworking with the pinion gear.

The cleaning body may further include a third part extending in the inward direction of the frame from the second part, the transfer motor may be installed in the third part.

The cleaning body may include first and second bodies facing the bottom of the mattress, and the first and second bodies are disposed on opposing sides of a central bracket.

The suction portion may be provided on an upper surface of the first and second bodies.

The cleaning body may include: a lower cleaning body facing the bottom of the mattress; and an upper cleaning body communicating with the lower cleaning body and facing an upper surface and a side surface of the mattress.

BRIEF DESCRIPTION OF THE DRAWINGS

The accompanying drawings, which are included to provide a further understanding of the disclosure and are incorporated in and constitute a part of this application, illustrate embodiments of the disclosure and together with the description serve to explain the principle of the disclosure. In the drawings.

DETAILED DESCRIPTION OF THE DISCLOSURE

Figure 1:
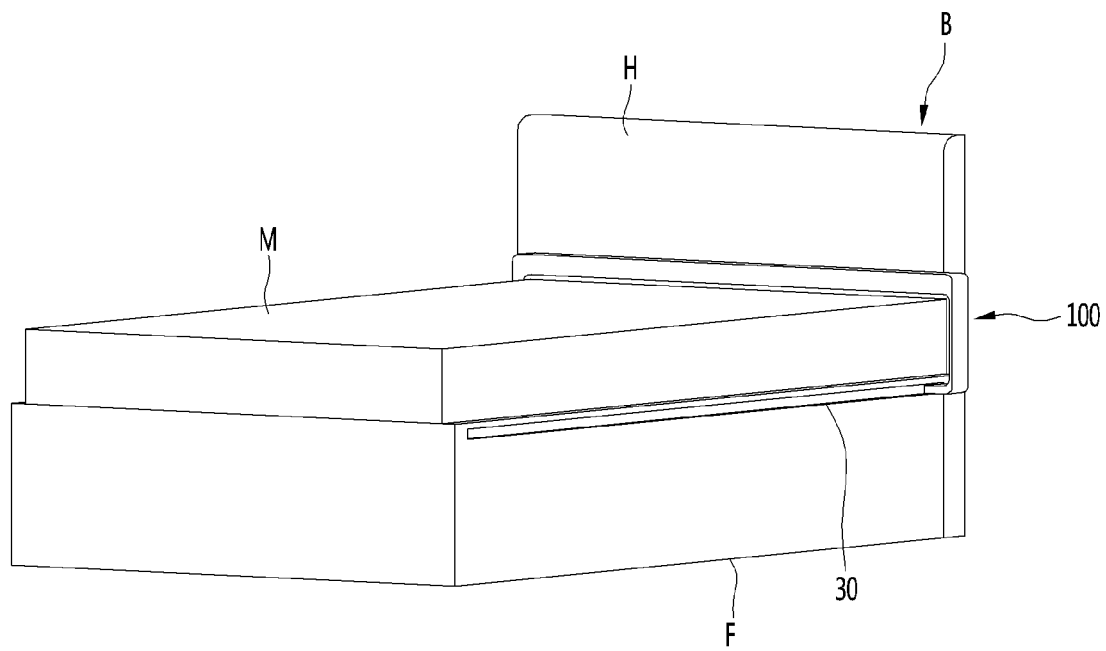
FIG. 1 is a perspective view showing a bed installed with a cleaner according to a first embodiment of the present disclosure.

Hereinafter, exemplary embodiments of the present disclosure will be described in detail with reference to the accompanying drawings. In adding reference numerals for elements in each figure, it should be noted that like reference numerals already used to denote like elements in other figures may be used for elements wherever possible. Moreover, detailed descriptions related to well-known functions or configurations may be omitted in order not to unnecessarily obscure subject matters of the present disclosure.

In describing the elements of the present disclosure, terms such as first, second, A, B, (a), (b), etc., may be used. Such terms are used for merely discriminating the corresponding elements from other elements and the corresponding elements are not limited in their essence, sequence, or precedence by the terms. It will be understood that when an element or layer is referred to as being "on" or "connected to" another element or layer, it may be directly on or directly connected to the other element or layer, or intervening elements or layers may be present.

Figure 2:
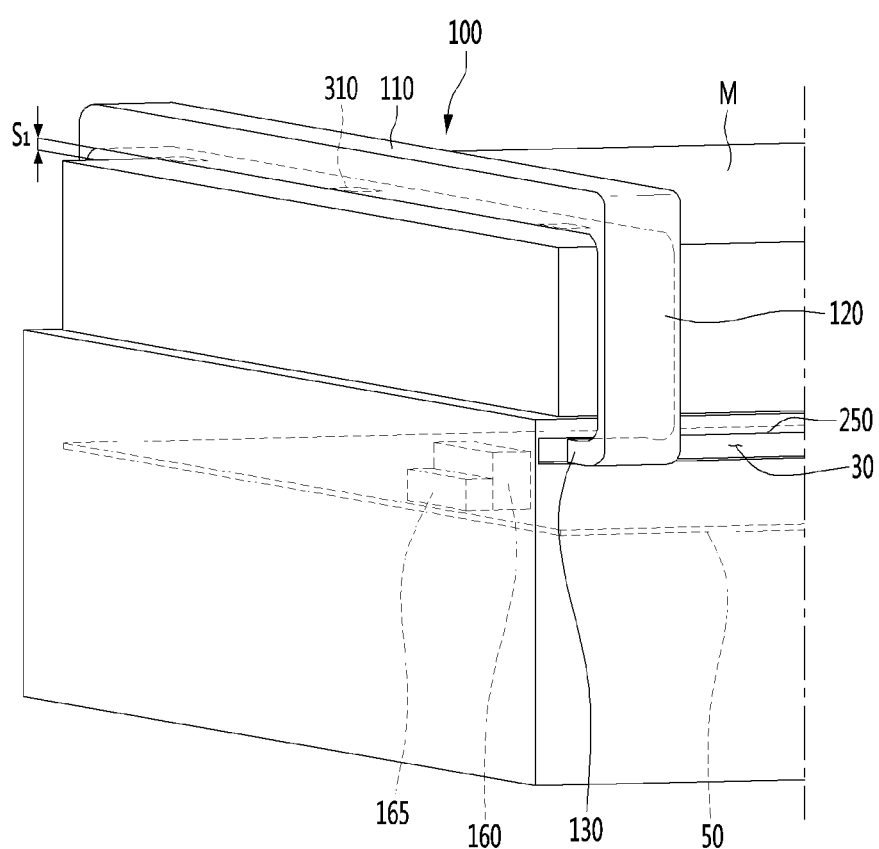
FIG. 2 is a view showing a state where a cleaner has moved to a lower end of a bed.
Figure 3:
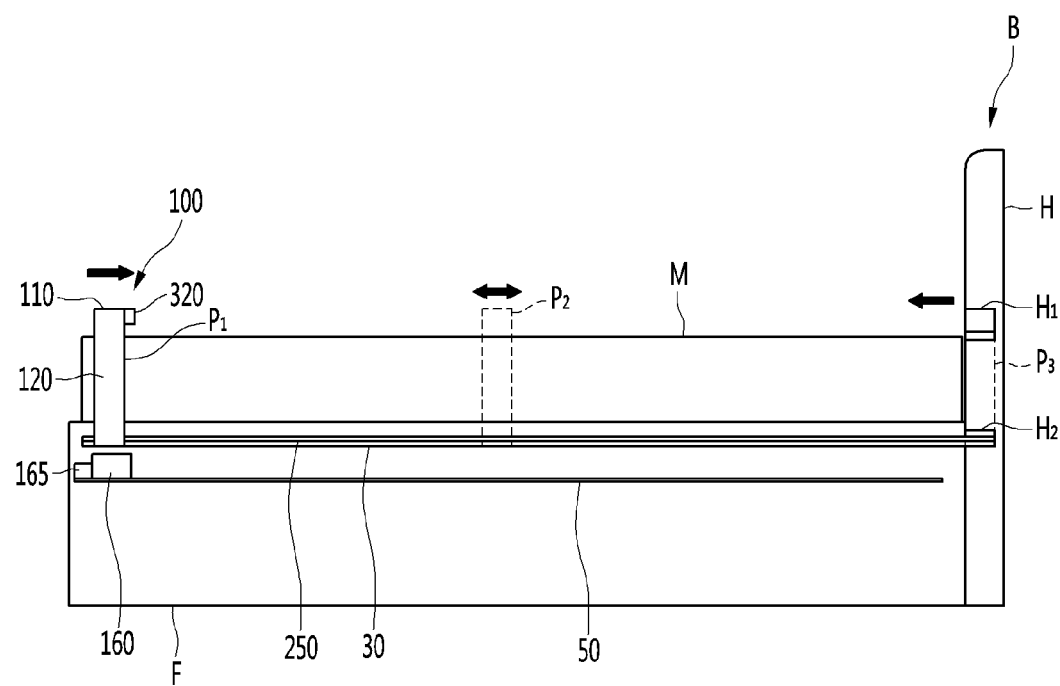
FIG. 3 is a side view showing a bed with a cleaner according to the first embodiment of the present disclosure.

FIG. 1 is a perspective view showing a bed in which a cleaner is installed according to a first embodiment of the present disclosure, FIG. 2 is a view showing a state where the cleaner according to the first embodiment of the present disclosure has moved to a lower end of the bed, and FIG. 3 is a side view showing a bed in which a cleaner is installed according to the first embodiment of the present disclosure.

Referring to FIGS. 1 and 2, a cleaner 100 for a bed (hereinafter, referred to as a "cleaner") according to the first embodiment of the present disclosure may be installed at a bed B. The bed B may include a lower frame F, a mattress M placed on the frame F, and a head portion H provided at an upper end of the frame F. The head portion H may extend from an upper side of the mattress M. The mattress M may have a rectangular parallelepiped shape having a predetermined vertical thickness.

For purposes of this disclosure, the following directions are defined. A portion where the head portion H is positioned may be defined as a "front portion" of the bed B and the opposite side may be defined as a "rear portion" of the bed B. Also between two positions, the position closer to the head portion H may be defined as a "front" and the position closer to the opposite side may be defined as a "rear".

The cleaner 100 may be configured to surround an upper surface and both side surfaces of the mattress M. For example, the cleaner 100 may be positioned adjacent to the surface of the mattress M and may be provided to be movable in a longitudinal direction of the bed B.

The bed B may be formed with a guide groove 30 to guide a movement path of the cleaner 100. The guide groove 30 may be formed such that at least part of a lateral portion of the frame F is penetrated therethrough, and may extend in a longitudinal direction. The guide groove 30 may be formed on both sides of the frame F.

Both side portions of the cleaner 100 may be inserted into the guide groove 30 and move in the longitudinal direction in which the guide groove 30 extends.

A rack 250 interworking with the cleaner 100 may be provided on an inner side of the guide groove 30. A transfer motor assembly 150 (see FIG. 7) of the cleaner 100 may work with the rack 250. Specifically, the pinion gear 154 of the transfer motor assembly 150 is gear-coupled with the rack 250, and the cleaner 100 may be moved in a front-rear direction as the pinion gear 154 and the rack 250 interwork with each other.

The cleaner 100 includes a cleaning body bent to surround the outer surface of the mattress M. An inner flow path 180 (see FIG. 10) through which dust sucked from the mattress M may flow may be formed in the cleaning body.

The cleaning body may include a first part 110 disposed adjacent to the upper surface of the mattress M and a second part 120 extending downward from both sides of the first part 110 and disposed adjacent to side surfaces of the mattress M.

A suction portion 113 (see FIG. 9) capable of sucking foreign matter or dust present in the mattress M may be formed on a bottom of the first part 110. In order to facilitate suction of the foreign matter or dust through the suction portion 113, a distance between the bottom of the first part 110 and the upper surface of the mattress M may be maintained at or below a set distance S1. For example, the set distance S1 may be formed in the range of 2 to 5 mm.

The cleaning body may further include a third part 130 extending from the second part 120 toward an inner direction of the guide groove 30. The third part 130 may be inserted into the guide groove 30. The transfer motor assembly 150 may be installed at an upper portion of the third part 130 (see FIG. 7).

By the configuration of the first to third parts 110, 120, and 130, the cleaning body may have a shape that is bent twice, for example, a cap shape or "C" shape.

A support plate 50 on which some of the components of the cleaner 100 are installed may be provided on an inner side of the frame F. An installation height of the support plate 50 may be lower than an upper end of the frame F.

A cleaning motor 160 for generating a suction force to the cleaner 100 and a dust box 165 for storing dust in the air flown in by the suction force of the cleaning motor 160 may be installed on the support plate 50. The cleaning motor 160 and the dust box 165 may be supported on an upper surface of the support plate 50.

The cleaner 100 may be moved linearly in a front-rear direction of the bed B. For example, referring to FIG. 3, the cleaner 100 may be positioned at a first position P1 adjacent to the rear side of the mattress M. The first position P1 may be a limit position at the rear of the cleaner 100.

The cleaner 100 may move forward from the first position P1 and may be positioned at a second position P2. The second position P2 may be a reference center position in the front-rear direction of the cleaner 100.

The cleaner 100 may move forward from the second position P2 and may be positioned at a third position P3. The third position P3 may be a position at which the cleaner 100 is inserted into the head portion H and may be a limit position at the front of the cleaner 100.

The head portion H may be provided with insertion portions H1 and H2 into which the cleaner 100 may be inserted. The insertion portions H1 and H2 may be recessed forward from a rear surface of the head portion H.

The insertion portions H1 and H2 may include a first insertion portion H1 and a second insertion portion H2 spaced apart in the longitudinal direction with respect to the head portion H. The first insertion portion H1 may be formed above the second insertion portion H2. The first part 110 of the cleaner 100 may be inserted into the first insertion portion H1 and the third part 130 of the cleaner 100 may be inserted into the second insertion portion H2.

When the cleaner 100 is at the third position P3, the cleaner 100 has moved outside of the mattress M, and thus the user may use the mattress M without any inconvenience. That is, the third position P3 is a limit position of the cleaner 100 at which the cleaner 100 is inserted into the head portion H, and the cleaner 100 is at the third position P3 when not in use.

And, in the case of cleaning the mattress M using the cleaner 100, the cleaner 100 may move from the third position P3 toward the first position P1 and clean the mattress M, while moving or reciprocating in the front-rear direction between the first position P1 and the third position P3.

In order to control the movement of the cleaner 100, the cleaner 100 may include sensors 310 and 320 for detecting state information or use information of the mattress M.

For example, among the sensors 310 and 320, a bottom sensor 310 may detect a distance between the first part 110 and the upper surface of the mattress M. The bottom sensor 310 may be a distance sensor, for example, that may be an infrared sensor. As described above, the distance between the bottom surface of the first part 110 and the upper surface of the mattress M may need to be maintained within the set distance S1.

A vertical height of the mattress M may vary for each manufacturer. In addition, when the mattress M is used for a long time, the upper surface of the mattress M may be recessed downward.

Figure 10:
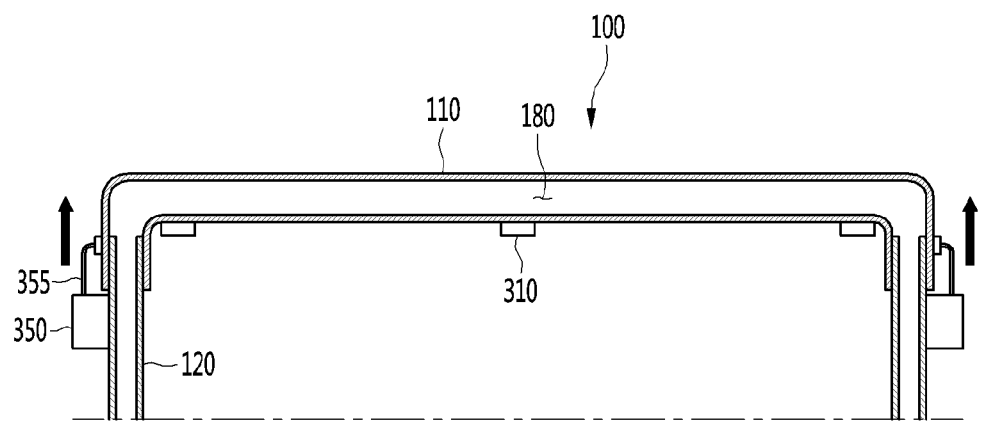
FIG. 10 is a cross-sectional view taken along line X-X' of FIG. 6.
Figure 11:
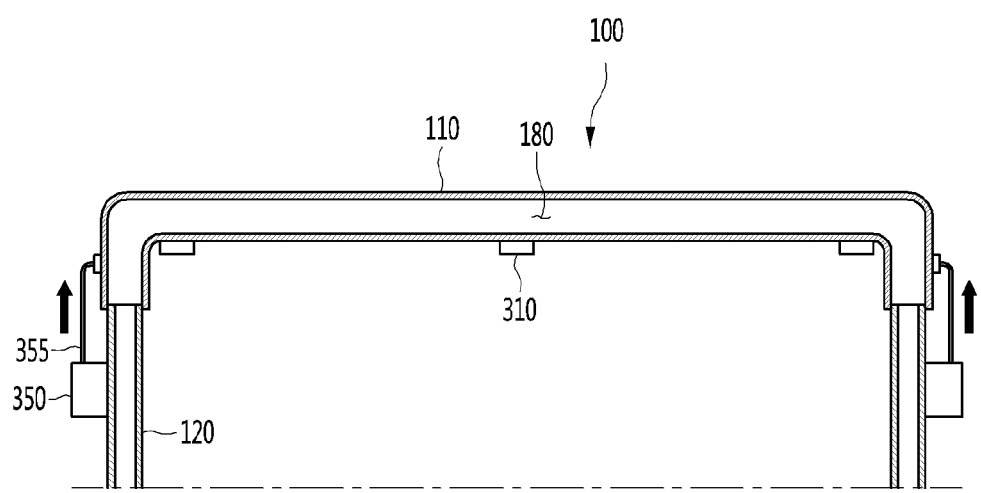
FIG. 11 is a cross-sectional view showing a state where the first part of the cleaner has moved upward with respect to a second part according to the first embodiment of the present disclosure.

Therefore, the distance between the upper surface of the mattress M and the bottom of the first part 110 may be detected using the bottom sensor 310 and a height of the first part 110 may be adjusted according to the detection result, that is, the distance between the first part 110 and the upper surface of the mattress M may be adjusted (see FIGS. 10 and 11).

The sensors 310 and 320 may further include a front sensor 320 that may be provided on a front surface of the first part 110 to detect the presence of an object on the mattress M. The object may be, for example, a human body or a stuff.

If the cleaner 100 is driven with an object present on the upper surface of the mattress M, smooth movement of the cleaner 100 through the control of the transfer motor assembly 150 may be interfered with. Therefore, in the present embodiment, it may be possible to determine whether an object is present on the upper surface of the mattress M by using the front sensor 320. The front sensor 320 may be a distance sensor and may be configured as an infrared sensor, for example.

When it is detected that an object is present on the upper surface of the mattress M through the front sensor 320, the operation of the cleaner 100 may be stopped and an alarm sound may be activated.

Figure 4:
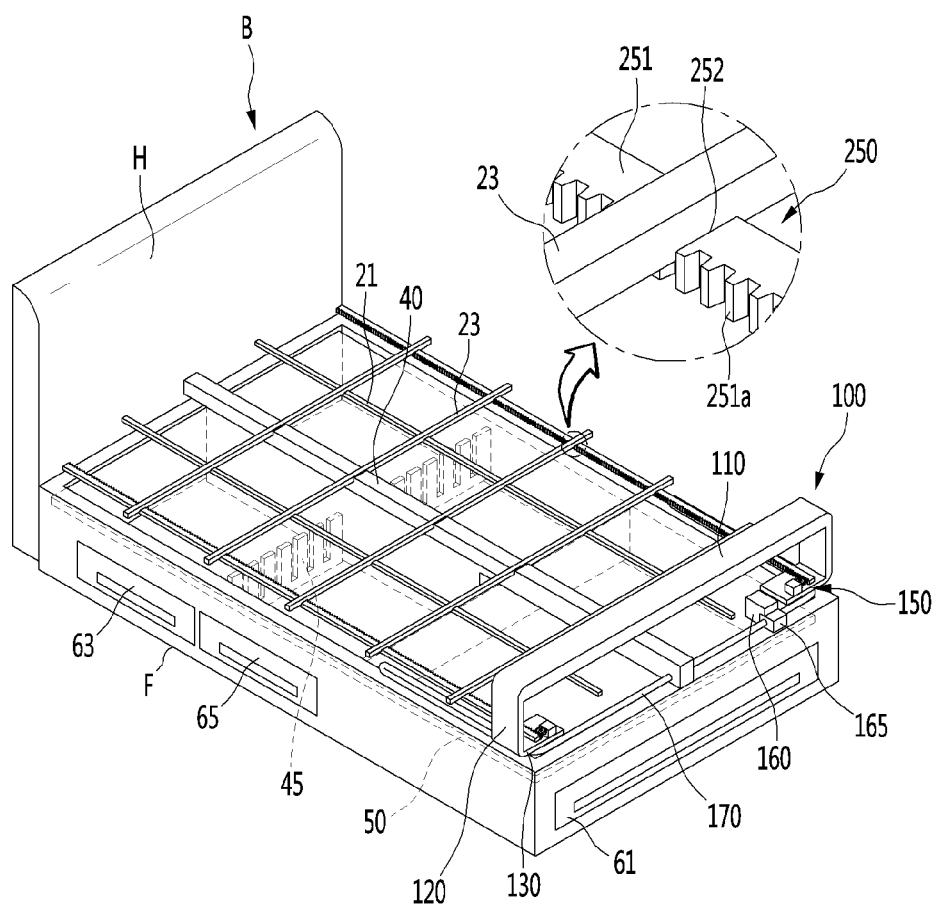
FIG. 4 is a perspective view showing a state of a bed in which a cleaner is installed and a mattress is removed according to the first embodiment of the present disclosure.
Figure 5:
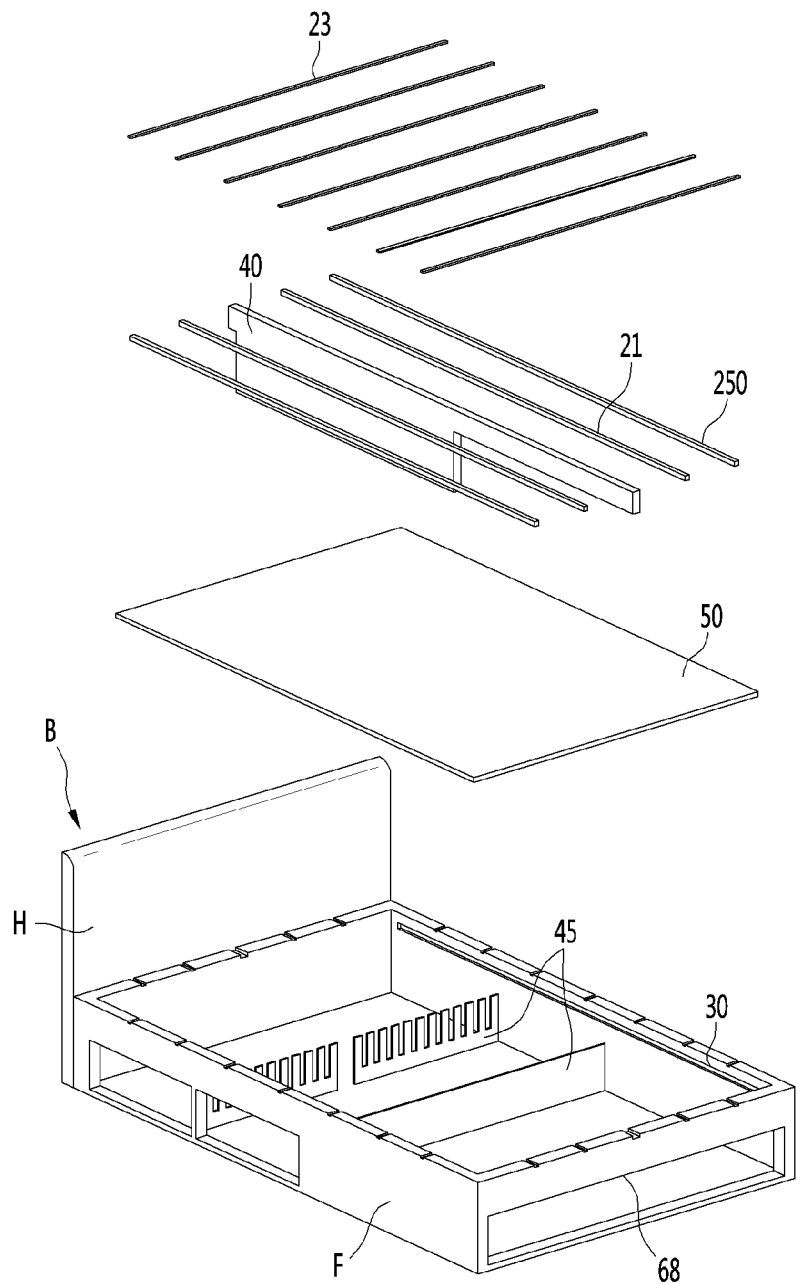
FIG. 5 is an exploded perspective view showing a configuration of a bed in which a cleaner is installed according to the first embodiment of the present disclosure.

FIG. 4 is a perspective view showing a state of a bed in which a cleaner is installed and a mattress is removed according to the first embodiment of the present disclosure and FIG. 5 is an exploded perspective view showing a configuration of a bed in which a cleaner is installed according to the first embodiment of the present disclosure.

Referring to FIGS. 4 and 5, the cleaner 100 according to the first embodiment of the present disclosure may be installed at the bed B including a plurality of support frames 21 and 23 and brackets 40 and 45.

For example, the bed B includes the frame F with an open upper portion and the brackets 40 and 45 provided inside the frame F and supporting the mattress M. The brackets 40 and 45 may include a central bracket 40 positioned at the center of an inner space of the frame F and a lower bracket 45 positioned to be spaced apart in the front-rear direction in the inner space of the frame F. The lower bracket 45 may extend in a transverse direction.

The central bracket 40 and the lower bracket 45 may be arranged to cross each other and coupled. The lower bracket 45 may be positioned below the support plate 50, and the central bracket 40 may extend upward through the support plate 50. That is, a part of the central bracket 40 may be disposed below the support plate 50 and the other part may be disposed above the support plate 50.

The bed B may further include a plurality of support frames 21 and 23 positioned above the frame F and arranged in a grid shape. The plurality of support frames 21 and 23 may be positioned above the brackets 40 and 45 and may support the mattress M.

The plurality of support frames 21 and 23 may include a plurality of main support frames 21 disposed to be spaced apart from each other in a transverse direction and extending in a front-rear direction and a plurality of sub-support frames 23 disposed to be spaced apart from each other in the front-rear direction and extending in the transverse direction. The plurality of sub-support frames 23 may be placed on the plurality of main support frames 21. A thickness and strength of the main support frame 21 may be greater than a thickness and strength of the sub-support frame 23.

The main support frame 21 may be disposed at a height corresponding to a height of an upper end of the central bracket 40. The sub-support frame 23 may be placed in a frame recess 41 of the central bracket 40. The frame recess 41 may be a recess depressed from an upper surface of the central bracket 40.

The rack 250 may be provided on both inner side surfaces of the frame F and may be disposed on both sides of the plurality of main support frame 21. In addition, the rack 250 may extend in the front-rear direction.

The plurality of sub-support frames 23 may be placed on the rack 250. For example, the rack 250 may include a rack body 251 extending in the front-rear direction. The rack body 251 may extend from the front end of the frame F to a rear end thereof.

The rack 250 may further include a frame seating portion 252 formed on an upper surface of the rack body 251 and allow the sub-support frame 23 to be seated or inserted thereon. The rack 250 may include a gear portion 251a formed on a side surface of the rack body 251 and may include a plurality of gear teeth. The gear portion 251a may be linked to a pinion gear 154 of the transfer motor assembly 150 (see FIG. 7).

A plurality of drawers 61, 63, and 65 may be provided to be drawn out in the frame F. The plurality of drawers 61, 63, and 65 may be disposed in an inner space of the frame F partitioned by the brackets 40 and 45. A plurality of drawer insertion holes 68 through which the plurality of drawers 61, 63, and 65 may be drawn may be formed in the frame F.

For example, the plurality of drawers 61, 63, and 65 may include a first drawer 61 provided to be drawn out at a rear portion of the frame F. The first drawer 61 may be provided to be drawn out backward, and a horizontal width of the first drawer 61 may be similar to a horizontal width of the frame F.

The plurality of drawers 61, 63, and 65 may include second and third drawers 63 and 65 provided to be drawn out at side portions of the frame F. The second and third drawers 63 and 65 may be provided to be drawn out laterally, and the third drawer 65 may be disposed on the rear side of the second drawer 63.

The support plate 50 may be disposed in a space between the brackets 40 and 45 and the plurality of support frames 21 and 23. That is, the support plate 50 may be disposed above the brackets 40 and 45 and below the plurality of support frames 21 and 23.

The guide hole 30 of the frame F may be formed at a position higher than the support plate 50, and the third part 130 of the cleaner 100 may be inserted into the guide hole 30 and extend to the inner space of the frame F. Therefore, the third part 130 may be disposed at a position higher than the support plate 50.

The cleaning motor 160 and the dust box 165 may be installed at the support plate 50, and the transfer motor assembly 150 may be seated on the upper surface of the third part 150. A dust flow path 170 provided at the cleaner 100 may be disposed in a space between the brackets 40 and 45 and the plurality of support frames 21 and 23. Hereinafter, a detailed configuration of the cleaner 100 will be described with reference to the accompanying drawings.

Figure 6:
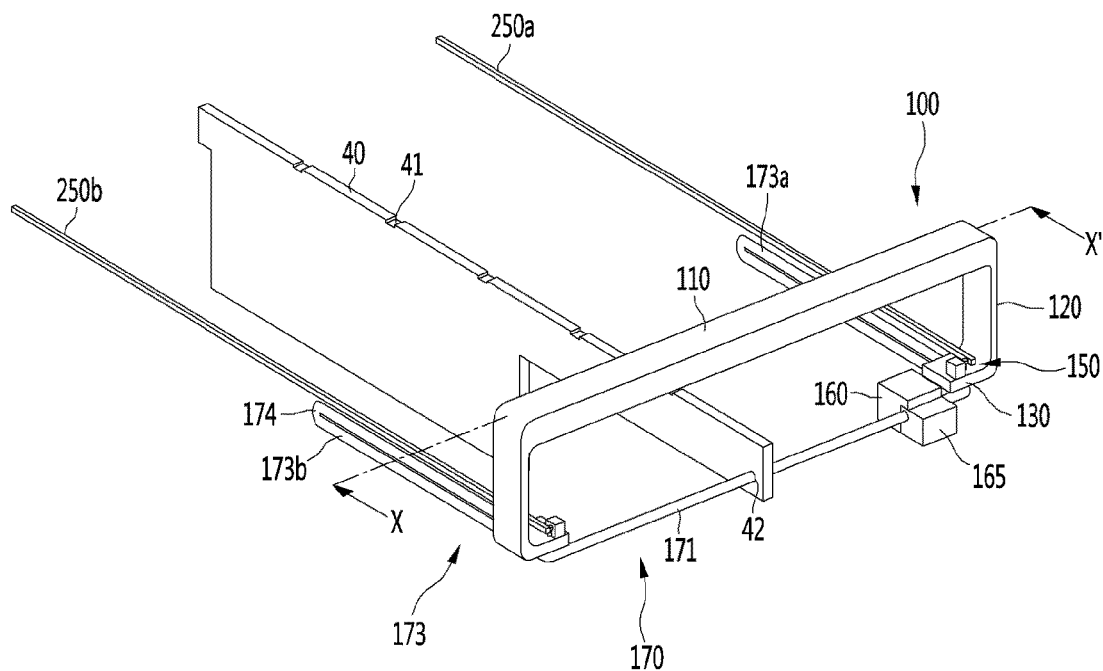
FIG. 6 is a perspective view showing a configuration of a cleaner according to the first embodiment of the present disclosure.
Figure 7:
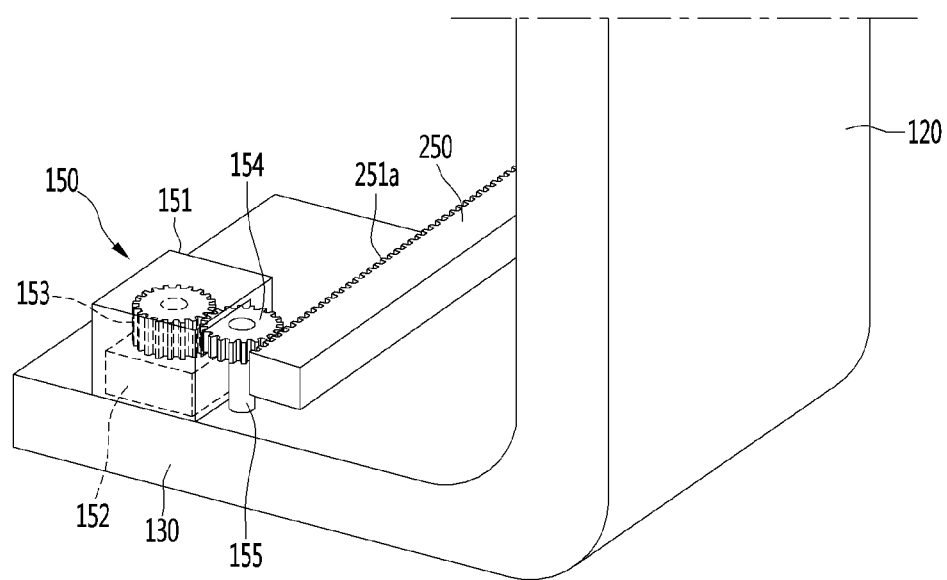
FIG. 7 is a perspective view showing a configuration of a transfer motor assembly according to the first embodiment of the present disclosure.
Figure 8:
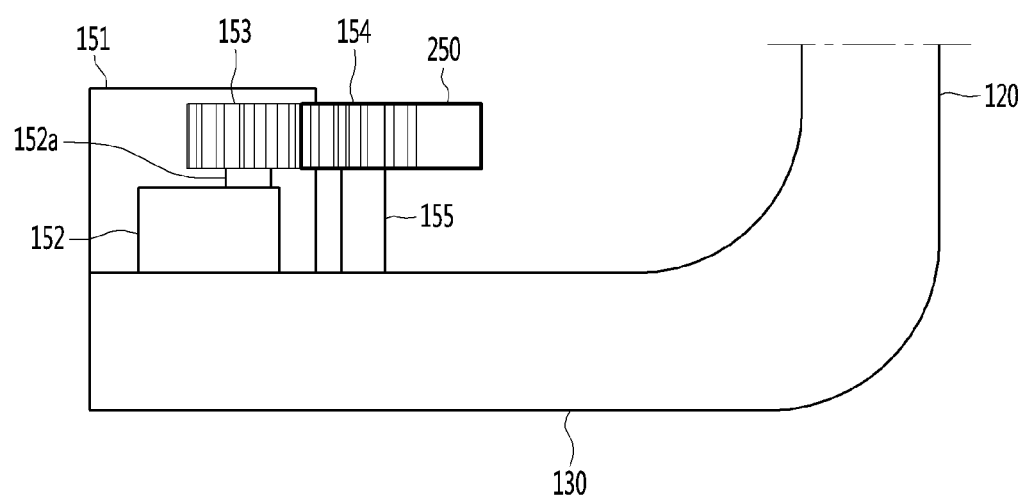
FIG. 8 is a side view showing a configuration of a transfer motor assembly according to the first embodiment of the present disclosure.
Figure 9:
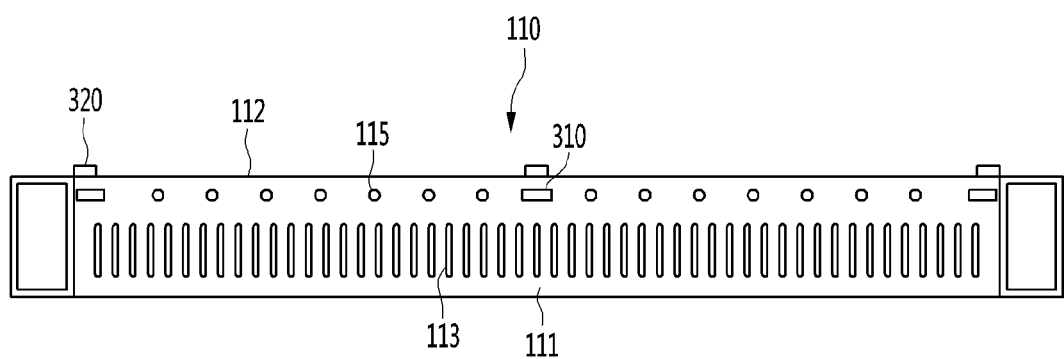
FIG. 9 is a view showing a configuration of a bottom of a first part of a main body of a cleaner according to the first embodiment of the present disclosure.

FIG. 6 is a perspective view showing a configuration of a cleaner according to the first embodiment of the present disclosure, FIG. 7 is a perspective view showing a configuration of a transfer motor assembly according to the first embodiment of the present disclosure, FIG. 8 is a side view showing a configuration of a transfer motor assembly according to the first embodiment of the present disclosure, and FIG. 9 is a view showing a configuration of a bottom of a first part of a main body of a cleaner according to the first embodiment of the present disclosure.

Referring to FIGS. 6 to 8, the cleaner 100 according to the first embodiment of the present disclosure may include cleaning bodies 110, 120, and 130 provided to be movable in a front-rear direction and sucking dust or foreign matters, a cleaning motor 160 generating suction force, a dust box 165 communicating with the cleaning bodies 110, 120, and 130 and storing dust or foreign matter, and a dust flow path 170 connecting the cleaning bodies 110, 120, 130 and the dust box 165.

The dust flow path 170 may be connected to the third part 130 of the cleaning body and extend to the dust box 165. That is, one end of the dust flow path 170 may be coupled to the third part 130, and the other end thereof may be coupled to the dust box 165.

For example, the dust flow path 170 may include a fixed flow path 171 coupled to the dust box 165 and extending in a transverse direction and a variable flow path 173 extending forward from both sides of the fixed flow path 171 and varied in length or shape. For example, the dust flow path 170 may be formed of a corrugated pipe that may be deformed. The fixed flow path 171 and the variable flow path 173 may be integrally formed.

The fixed flow path 171 may extend in the transverse direction through the central bracket 40 and may be coupled to the dust box 165. The central bracket 40 may have a flow path through a portion 42 through which the fixed flow path 171 is inserted.

The fixed flow path 171 may include a first flow path portion connected to the first variable flow path 173a and a second flow path portion connected to the second variable flow path 173b among the two variable flow paths 173. The first flow path portion may be coupled to one side of the dust box 165, and the second flow path portion may be coupled to the other side of the dust box 165.

Dust flowing through the first variable flow path 173*a* may be sucked into the dust box 165 through the first flow path portion, and dust flowing through the second variable flow path 173*b* may be sucked into the dust box 165 through the second flow path portion. The dust box 165 communicates with the cleaning motor 160, and air from which foreign matter is separated through the dust box 165 may be discharged to the outside via the cleaning motor 160.

Two variable flow paths 173, that is, the first and second variable flow paths 173*a* and 173*b*, may be connected to two third parts 130, respectively. The variable flow path 173 may be folded and arranged in two stages. Specifically, at least part of the variable flow path 173 may be folded to form a folded portion 174.

When the cleaner 100 moves in the front-rear direction, a position of the folded portion 174 moves in the front-rear direction, and in this process, the variable flow path 173 may be deformed. By the configuration and operation of the variable flow path 173, the dust sucked through the cleaner 100 may be easily sucked into the cleaning motor 160 even if the cleaner 100 is moved.

The rack 250 may include a first rack 250*a* disposed on one side of the frame F and a second rack 250*b* disposed on the other side. The cleaner 100 may include two transfer motor assemblies 150 to correspond to the first and second racks 250*a* and 250*b*. The two transfer motor assemblies 150 may be installed on two third parts 130 of the cleaning body.

The transfer motor assembly 150 may include a motor housing 151 provided on an upper surface of the third part 130, a transfer motor 152 installed in the motor housing 151, and a motor gear 153 coupled to the transfer motor 152. The motor gear 153 may be coupled to a motor shaft 152*a* of the transfer motor 152.

The transfer motor assembly 150 may further include a pinion gear 154 interworking with the motor gear 153. The pinion gear 154 may be positioned outside the motor housing 151 and may be gear-coupled to the gear portion 251*a* of the rack 250.

The pinion gear 154 may be coupled to the third part 130 through a gear support 155. The gear support 155 may extend upward from an upper surface of the third part 130 and may be coupled to the center of the pinion gear 154. The cleaning bodies 110, 120, and 130 may move in the front-rear direction as the rack 250 and the pinion gear 154 interwork with each other.

A configuration of the first part 110 of the cleaning body will be described. The cleaning body may be referred to as a "dust pipe" in that it guides a flow of dust. Referring to FIG. 9, the first part 110 may extend in a transverse direction and may be positioned adjacent to the upper surface of the mattress M.

A suction portion 113 for sucking dust or foreign matter may be formed on a bottom portion 111 of the first part 110, that is, a surface facing the upper surface of the mattress M. The suction portion 113 may be provided in plurality and may be arranged in a transverse direction. When the cleaning motor 160 is driven, a suction force acts on the suction portion 113, and foreign matter or dust existing in the mattress M may be sucked in.

The first part 110 may be provided with an irradiation source 115 for removing harmful organisms or germs present in the mattress M. For example, the irradiation source 115 may include an ultraviolet lamp. The irradiation source 115 may be provided in plurality on the bottom portion 111 and arranged in the transverse direction.

A bottom sensor 310 may be installed on the bottom portion 111 of the first part 110. The bottom sensor 310 may detect a distance between the bottom portion 111 and the upper surface of the mattress M. When the detected distance is greater than or equal to the set distance, the first part 110 may be moved downward. The bottom sensor 310 may be provided in plurality, for example, at the central portion and both side portions of the bottom portion 111.

A front sensor 320 for detecting whether a certain obstacle is present on the mattress M may be provided at a front portion 112 of the first part 110. When it is detected that an obstacle exists through the front sensor 320, movement of the cleaner 100 may be stopped and an alarm sound may be activated. The front sensor 320 may be provided in plurality, for example, at the central portion and both side portions of the front portion 112.

FIG. 10 is a cross-sectional view taken along line X-X' of FIG. 6, and FIG. 11 is a cross-sectional view showing a state where the first part of the cleaner has moved upward with respect to a second part according to the first embodiment of the present disclosure.

Referring to FIG. 10, the cleaner 100 according to the first embodiment of the present disclosure may further include the first part 110 provided to be movable in a longitudinal direction and the second part 120 extending downward from opposing sides of the first part 110.

For example, an upper portion of the second part 120 may be inserted into the first part 110. As another example, both sides of the first part 110 may be inserted into the second part 120.

The cleaner 100 may further include a vertical motor 350 providing a driving force for vertical movement of the first part 110 and a slider 355 connected to the vertical motor 350 and pushing up the first part 110.

The vertical motor 350 may be installed on a side portion of the second part 120, and the slider 355 may extend from the vertical motor 350 and may be coupled to the first part 110. For example, the slider 355 may extend upward from the vertical motor 350 and may be coupled to a side surface of the first part 110.

The vertical motor 350 and the slider 355 may be provided at the two second parts 120, respectively, and may be synchronized with each other to smoothly control the vertical movement of the first part 110.

When the distance between the upper surface of the mattress M and the bottom of the first part 110 is recognized to be the set distance S1 (See FIG. 2) or greater through the bottom sensor 310 provided at the bottom portion 111 of the first part 110, the vertical motor 350 may be driven and the slider 355 is drawn into the vertical motor 350 and the first part 110 may move downward.

Meanwhile, if the distance between the upper surface of the mattress M and the bottom of the first part 110 is recognized to be less than the set distance S1, the vertical motor 350 may be driven and the slider 355 is drawn out from the vertical motor 350 so that the first part 110 may move upward.

Another embodiment is proposed.

In the first embodiment, it is described that the suction portion 113 and the irradiation source 115 are formed at the bottom portion 111 of the first part 110. In addition, the suction portion 113 and the irradiation source 115 may be provided on an inner surface of the second part 120. Therefore, foreign matter present on the side surface of the mattress M may be sucked through the suction portion of the second part 120, and the side of the mattress M may be sterilized through the irradiation source of the second part 120.

Figure 12:
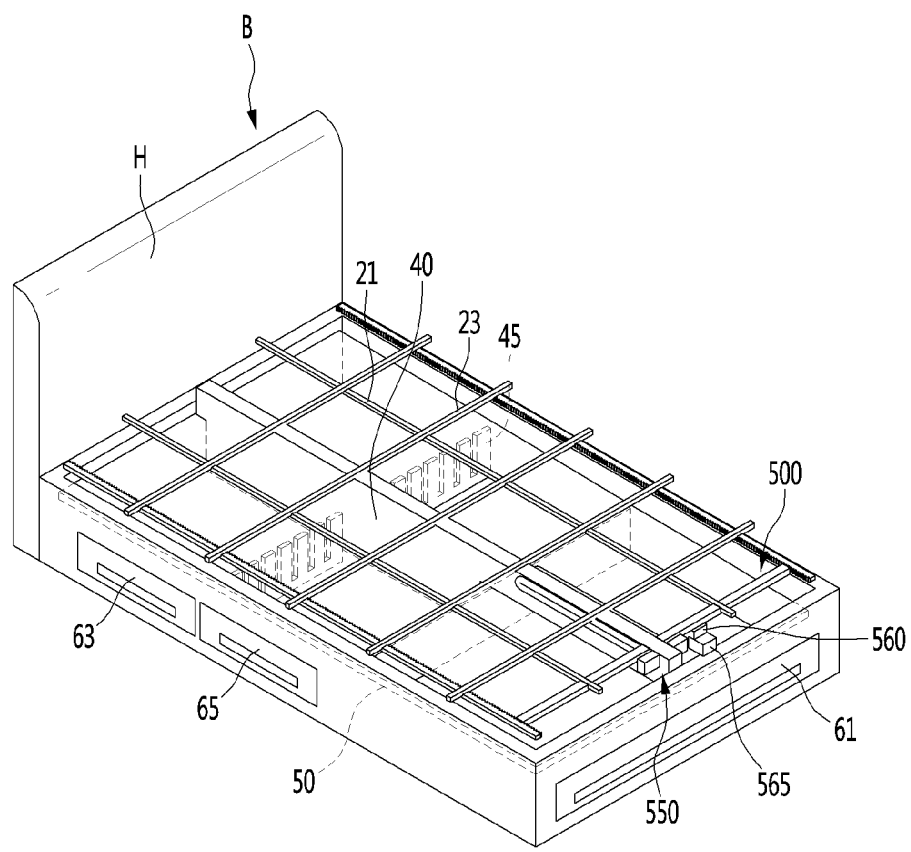
FIG. 12 is a perspective view showing a state of a bed in which a cleaner is installed and a mattress is removed according to a second embodiment of the present disclosure.
Figure 13:
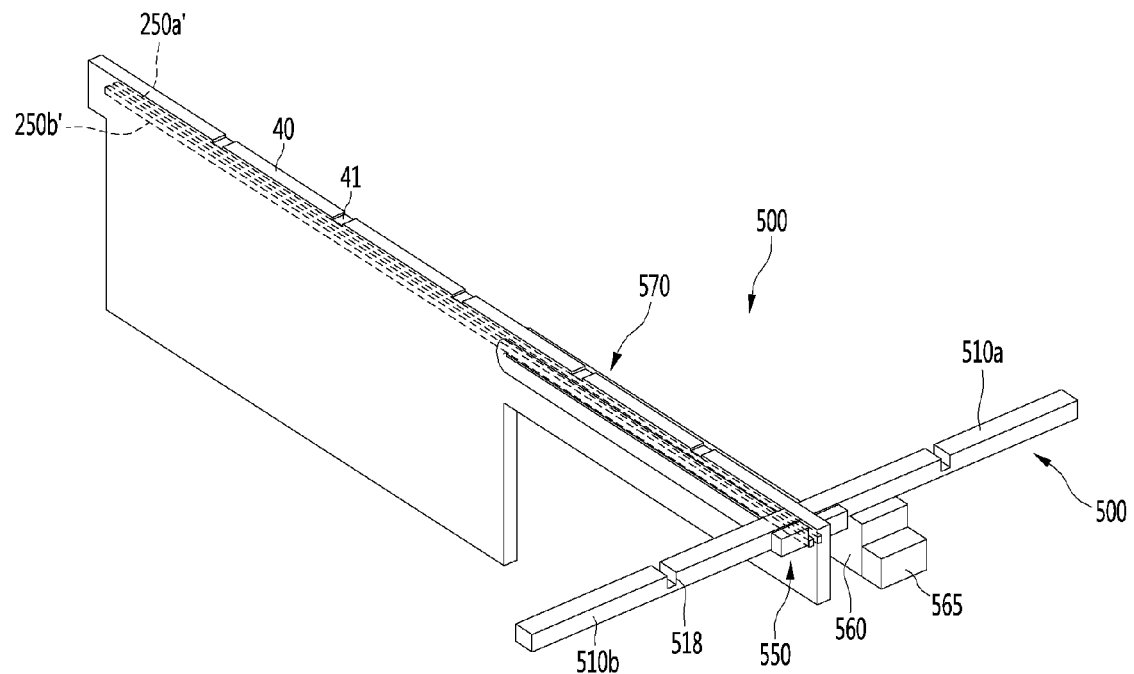
FIG. 13 is a perspective view showing a configuration of a cleaner according to a second embodiment of the present disclosure.
Figure 14:
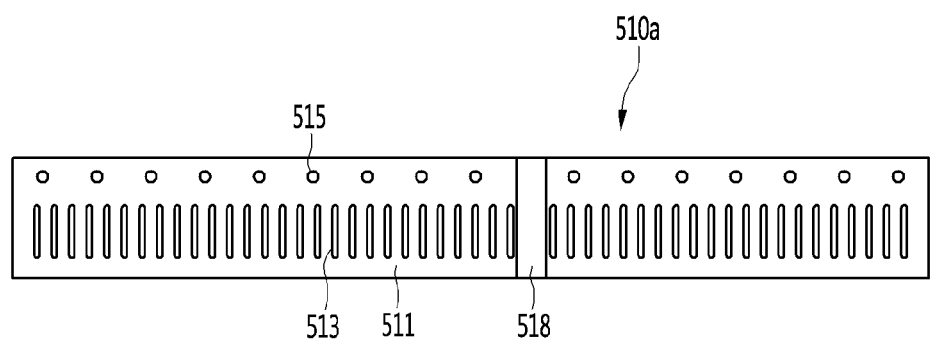
FIG. 14 is a view showing a configuration of a bottom of a first part of a main body of a cleaner according to the second embodiment of the present disclosure.
Figure 15:
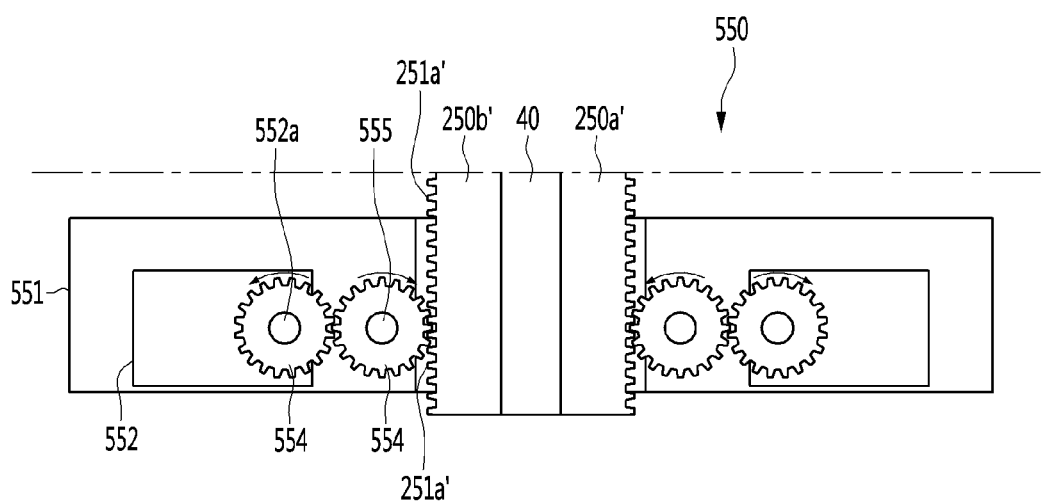
FIG. 15 is an internal view showing a configuration of a transfer motor assembly according to the second embodiment of the present disclosure.
Figure 16:
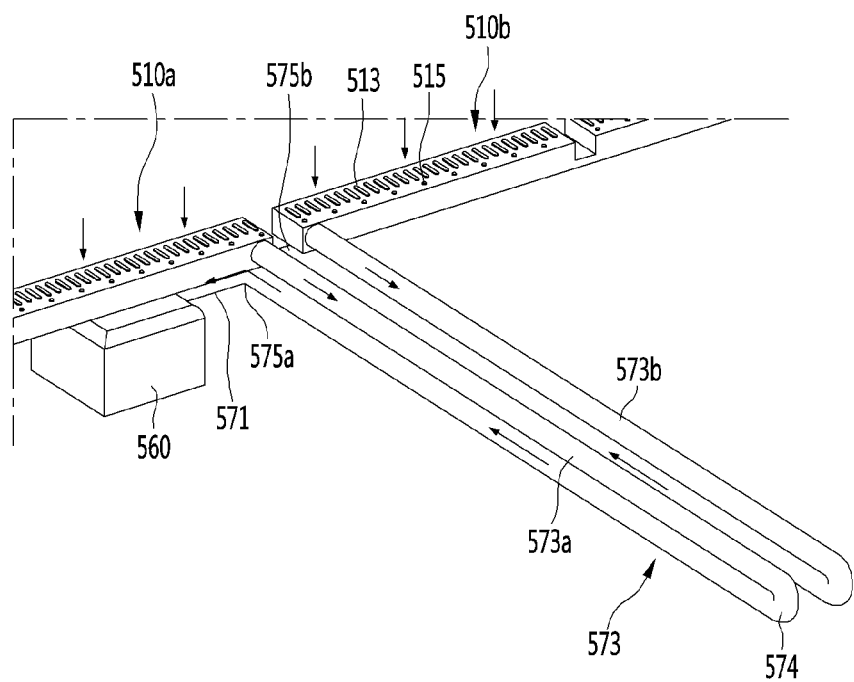
FIG. 16 is a view showing a flow of sucked dust in the cleaner according to the second embodiment of the present disclosure.

FIG. 12 is a perspective view showing a state of a bed in which a cleaner is installed and a mattress is removed according to a second embodiment of the present disclosure, FIG. 13 is a perspective view showing a configuration of a cleaner according to a second embodiment of the present disclosure, FIG. 14 is a view showing a configuration of a bottom of a first part of a main body of the cleaner according to the second embodiment of the present disclosure, FIG. 15 is an internal perspective view showing a configuration of a transfer motor assembly according to the second embodiment of the present disclosure, and FIG. 16 is a view showing a flow of sucked dust in the cleaner according to the second embodiment of the present disclosure.

Referring to FIGS. 12 to 16, a cleaner 500 according to the second embodiment of the present disclosure may be installed at a bed B provided with a plurality of support frames 21 and 23 and brackets 40 and 45. The plurality of support frames 21 and 23 and the brackets 40 and 45 may be coupled to the frame F. The brackets 40 and 45 may include a central bracket 40 and a lower bracket 45. The description of the first embodiment may be used as description of the plurality of support frames 21 and 23 and the brackets 40 and 45.

The bed B may include a first to third drawers 61, 63, and 65 provided to be retractable, and the description of the first embodiment may be used as description of the first to third drawers 61, 63, and 65.

The bed B may include a support plate 50, and the support plate 50 may be disposed in a space between the brackets 40 and 45 and the plurality of support frames 21 and 23. That is, the support plate 50 may be disposed above the brackets 40 and 45 and below the plurality of support frames 21 and 23.

The support plate 50 may be provided with a cleaning motor 560 and a dust box 565, a transfer motor assembly 550 may be coupled to the side of the central bracket 40. A dust flow path 570 provided in the cleaner 500 may be disposed in a space between the brackets 40 and 45 and the plurality of support frames 21 and 23.

The cleaner 500 may include a cleaning body 510 provided to be movable in a front-rear direction and sucking dust or foreign matter, a cleaning motor 560 generating a suction force, a dust box 565 communicating with the cleaning body 510 and storing dust or foreign matter, and a dust flow path 565 connecting the cleaning body 510 and the dust box 565 to each other.

The cleaning body 510 may be referred to as a "dust pipe" in that it guides a flow of dust. The cleaning body 510 may extend in the transverse direction and may be positioned adjacent to the bottom of the mattress M.

For example, the cleaning body 510 may include a first body 510a disposed on one side of the central bracket 40 and a second body 510b disposed on the other side. When the cleaner 500 is viewed from the front, the first body 510a may be disposed on the right side of the central bracket 40 and the second body 510b may be disposed on the left side of the central bracket 40.

The first and second bodies 510a and 510b may have the same configuration. Therefore, the first body 510a will be representatively described and the description thereof may be equally applicable to the second body 510b.

The first body 510a may extend in a transverse direction and have a shape of a bar that sucks dust from the mattress M.

The first body 510a has a frame insertion portion 518 on which the main support frame 21 may be placed. The frame insertion portion 518 may include a recess depressed downward from the upper surface portion 511 of the first body 510a.

The upper surface portion 511, that is, the surface facing the bottom of the mattress M may be formed with a suction portion 513 for sucking dust or foreign matter. The suction portion 513 may be provided in plurality and may be arranged in a transverse direction. When the cleaning motor 560 is driven, a suction force acts on the suction portion 513 to suck foreign matter or dust present in the mattress M.

The first body 510a may be provided with an irradiation source 515 for removing harmful organisms or germs present in the mattress M. For example, the irradiation source 515 may include an ultraviolet lamp. The irradiation source 515 may be provided in plurality on the upper surface portion 511 and arranged in the transverse direction.

The dust flow path 570 may extend from the first and second bodies 510a and 510b to the dust box 565. The dust flow path 570 may include a fixed flow path 571 coupled to the dust box 565 and extending in the transverse direction and a variable flow path 573 connected to the fixed flow path 571 and extending to the first and second bodies 510a and 510b.

The variable flow path 573 may extend forward from each of the first and second bodies 510a and 510b and is configured to be variable in length or shape. For example, the dust flow path 570 may be configured as a corrugated pipe that may be deformed. The fixed flow path 571 and the variable flow path 573 may be integrally formed.

The variable flow path 573 may include a first variable flow path 573a extending forward from the first body 510a and having a folded portion 574 and a second variable flow path 573b extending forward from the second body 510b and having the folded portion 574.

The first and second variable flow paths 573a and 573b may be folded at the folded portion 574 and arranged in two stages. When the cleaner 500 moves in the front-rear direction, the folded portion 574 may move in the front-rear direction, and in this process, the first and second variable flow paths 573a and 573b may be deformed. By the configuration and operation of the variable flow path 573, dust sucked through the cleaner 500 may be easily sucked into the dust box 565 even if the cleaner 500 is moved.

The fixed flow path 571 and the first and second variable flow paths 573a and 573b may be connected to each other. The first variable flow path 573a may join at a first junction 575a of the fixed flow path 571 and the second variable flow path 573b may join at a second junction 575b of the fixed flow path 571.

Referring to FIG. 16, when the cleaning motor 560 is driven, suction force acts on the first and second bodies 510a and 510b and dust or foreign matter of the mattress M may be sucked into the first and second bodies 510a and 510b by the suction force.

Dust or foreign matter sucked into the first and second bodies 510a and 510b flows through the first and second variable flow paths 573a and 573b, respectively, and flows into the fixed flow path 571 through the first and second joints 575a and 575b. Further, the dust or foreign matter flowed through the fixed flow path 571 is stored in the dust box 565, and air from which the dust or foreign matter is separated may be discharged to the outside via the cleaning motor 560.

Racks 250a' and 250b' may be provided on opposing side surfaces of the central bracket 40. For example, the racks 250a' and 250b' may include a first rack 250a' disposed on one side of the central bracket 40 and a second rack 250b' disposed on the other side of the central bracket 40.

The cleaner 500 may include two transfer motor assemblies 550 corresponding to the first and second racks 250a' and 250b'. The two transfer motor assemblies 550 may be coupled to rear surfaces of the first and second bodies 510a and 510b, respectively. Hereinafter, the transfer motor assembly 550 coupled to the first body 510a will be mainly described and the same description may be equally applicable to the transfer motor assembly 550 coupled to the second body 510b.

The transfer motor assembly 550 may include a motor housing 551 provided on a rear surface of the first body 510a, a transfer motor 552 installed in the motor housing 551, and a motor gear 553 coupled to motor 552. The motor gear 553 may be coupled to a motor shaft 552a of the transfer motor 152.

The transfer motor assembly 550 may further include a pinion gear 554 interworking with the motor gear 553. At least a portion of the pinion gear 554 may be positioned outside the motor housing 551 and may be gear-coupled to a gear portion 251a' of the rack 250a'.

The pinion gear 554 may be coupled to the motor housing 551 through a gear support 555. The gear support 555 may extend upward from the bottom of the motor housing 551 and may be coupled to the center of the pinion gear 554. The cleaning bodies 510a and 510b may move in a front-rear direction as the first racks 250a' and 250b' interwork with the pinion gear 554.

Figure 17:
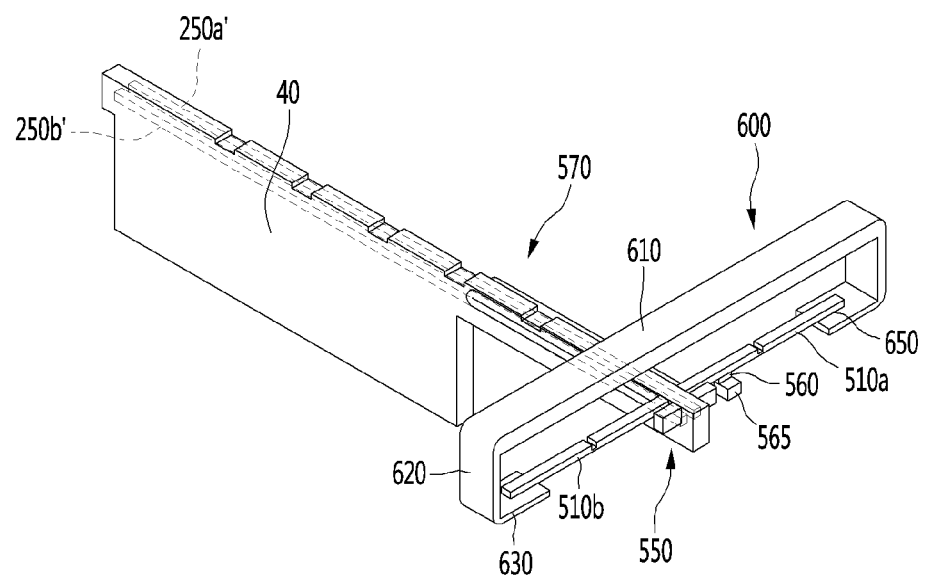
FIG. 17 is a perspective view showing a configuration of a cleaner according to a third embodiment of the present disclosure.

FIG. 17 is a perspective view showing a configuration of a cleaner according to a third embodiment of the present disclosure.

Referring to FIG. 17, a cleaner according to the third embodiment of the present disclosure may be configured by coupling the cleaning bodies 510a and 510b described in the second embodiment and the cleaning body 600 described in the first embodiment.

The transfer motor assembly 550 may be provided to move the cleaner according to the present embodiment, and a description thereof is the same as the description of the transfer motor assembly 550 of the second embodiment. In addition, a cleaning motor 560, a dust box 565, and a dust flow path 570 may be provided to store dust sucked through the cleaning body in the dust box, and a description thereof is the same as the description of the transfer motor assembly 550 of the second embodiment.

A structure of the cleaning body 600 may be the same as a configuration of the cleaning bodies 110, 120, and 130 described in the first embodiment. For example, the cleaning body 600 may include a first part 610, a second part 620, and a third part 630. The description of the first to third parts 610, 620, and 630 is the same as the description of the first to third parts 110, 120, and 130 of the first embodiment.

The cleaning bodies 510a and 510b may be coupled to both sides of the cleaning body 600, that is, the two third parts 630. For example, the first and second cleaning bodies 510a and 510b may be coupled to upper surfaces of the two third parts 630.

The third part 630 may include a connection portion 650 connected to the first and second cleaning bodies 510a and 510b. Through the connection portion 650, the third part 630 and the first and second cleaning bodies 510a and 510b may communicate with each other. For example, the connection portion 650 may be formed to penetrate through at least a portion of the upper surface of the third part 630. A hole connected to the connection portion 650 may be formed on the bottoms of the first and second cleaning bodies 510a and 510b. Therefore, when the cleaning motor 560 is driven, a suction force may act on the first and second cleaning bodies 510a and 510b and the cleaning body 600.

The cleaning body 510a and 510b may be disposed adjacent to the bottom of the mattress M to suck dust or foreign matter, and the cleaning body 600 may be disposed adjacent to the upper surface of the mattress M to suck in dust or foreign matter. According to this configuration, there is an advantage that dust or foreign matter may be sucked from the bottom and the upper surface of the mattress M.

For convenience of description, the cleaning bodies 510a and 510b may be referred to as "lower cleaning bodies" and the cleaning body 600 may be referred to as an "upper cleaning body".

According to the cleaner for a bed according to the embodiment of the present disclosure, since the cleaner is positioned adjacent to the surface of the bed mattress, cleaning efficiency of the mattress may be increased and the volume of the cleaner may be reduced.

Since the user can use the bed even when the cleaner is installed on the bed, there is no need to attach or remove the cleaner to or from the bed each time the cleaner is used.

Since the cleaner may perform cleaning, while moving up and down with reference to the longitudinal direction of the mattress of the bed, it is possible to evenly clean the entire surface of the mattress.

Since the dust suction port is provided on the bottom or upper surface of the cleaner, it is possible to easily suck dust present in the mattress.

Since the irradiation source for irradiating ultraviolet rays is disposed at the cleaner, it is possible to easily remove the harmful germs.

Since the cleaner is provided with the sensor for detecting an obstacle or the sensor for detecting a distance to the surface of the mattress, it is possible to easily adjust the height of the cleaner according to a detection result.

Since the main body of the cleaner is provided on the upper or lower surface of the mattress, dust and the like present on the surface of the mattress may be easily removed.

Since the dust flow path for guiding a flow of dust sucked into the cleaner is provided and the dust flow path includes the variable flow path varied in length or shape, dust may be easily sucked and flow even while the cleaner is moving.

Since the transfer guide device for guiding movement of the cleaner is provided, the cleaner may be smoothly moved.

It will be apparent to those skilled in the art that various modifications and variations may be made in the present disclosure without departing from the spirit or scope of the disclosures. Thus, it is intended that the appended claims and their equivalents cover the modifications and variations of this disclosure.

What is claimed is:

1. A cleaner for a bed for cleaning the bed including a frame on which a mattress is placed on the frame, the cleaner comprising:
   a cleaning body to be movable forward or backward with respect to a surface of the mattress, the cleaning body having a suction portion for sucking foreign matter from the mattress;
   a cleaning motor to communicate with the cleaning body and to generate a suction force;
   a dust box connected to the cleaning motor to store the foreign matter sucked in through the suction portion;

a transfer motor provided on one side of the cleaning body to generate a driving force for moving the cleaning body;
a vertical motor provided at the cleaning body to provide a driving force for moving a first part upward or downward; and
a slider connected to the vertical motor and the first part.

2. The cleaner of claim 1, wherein the cleaning body comprises:
the first part extending horizontally with respect to an upper surface of the mattress; and
a second part extending vertically from both sides of the first part for facing side surfaces of the mattress.

3. The cleaner of claim 2, wherein
the first part is coupled to the second part and movable upward or downward.

4. The cleaner of claim 2, wherein
the suction portion is provided at a bottom portion of the first part.

5. The cleaner of claim 2, wherein
an irradiation source for sterilizing the mattress is provided at a bottom portion of the first part.

6. The cleaner of claim 2, further comprising:
a pinion gear connected to the transfer motor; and
a rack interworking with the pinion gear.

7. The cleaner of claim 1, further comprising:
a bottom sensor provided at a bottom portion of the first part to sense a distance between the mattress and the first part,
wherein the vertical motor is driven based on a result sensed by the bottom sensor.

8. The cleaner of claim 1, further comprising:
a front sensor provided on a front surface portion of the first part to sense whether an object is present at the mattress,
wherein the transfer motor is driven based on a result sensed by the front sensor.

9. The cleaner of claim 1, further comprising:
a dust flow path connecting the cleaning body and the dust box.

10. The cleaner of claim 1, wherein
the cleaning body comprises first and second bodies disposed to face a bottom of the mattress.

11. The cleaner of claim 10, further comprising:
a central bracket for disposing at an inner side of the frame and supporting the mattress,
wherein the first and second bodies are disposed on opposing sides of the central bracket.

12. The cleaner of claim 11, further comprising:
racks provided on opposing sides of the central bracket, and
the first and second bodies move in a front-rear direction along the racks, respectively.

13. The cleaner of claim 10, wherein
the transfer motor includes a first transfer motor and a second transfer motor, and
the first transfer motor and the second transfer motor are provided at the first and second bodies, respectively.

14. The cleaner of claim 10, wherein
the suction portion is provided on an upper surface of the first and second bodies.

15. The cleaner of claim 1, wherein
the cleaning body comprises:
a lower cleaning body disposed to face a bottom of the mattress; and
an upper cleaning body communicating with the lower cleaning body and disposed to face an upper surface and a side surface of the mattress.

16. A cleaner for a bed for cleaning the bed including a frame on which a mattress is placed on the frame, the cleaner comprising:
a cleaning body to be movable forward or backward with respect to a surface of the mattress, the cleaning body having a suction portion for sucking foreign matter from the mattress;
a cleaning motor to communicate with the cleaning body and to generate a suction force;
a dust box connected to the cleaning motor to store the foreign matter sucked in through the suction portion;
a transfer motor provided on one side of the cleaning body to generate a driving force for moving the cleaning body; and
a dust flow path connecting the cleaning body and the dust box,
wherein the dust flow path includes a variable flow path changable in shape as the cleaning body moves forward or backward.

17. The cleaner of claim 16, wherein
the variable flow path comprises a folded portion, and
a position of the folded portion changes as the cleaning body moves forward or backward.

18. A cleaner for a bed for cleaning the bed including a frame on which a mattress is placed on the frame, the cleaner comprising:
a cleaning body to be movable forward or backward with respect to a surface of the mattress, the cleaning body having a suction portion for sucking foreign matter from the mattress;
a cleaning motor to communicate with the cleaning body and to generate a suction force;
a dust box connected to the cleaning motor to store the foreign matter sucked in through the suction portion; and
a transfer motor provided on one side of the cleaning body to generate a driving force for moving the cleaning body,
wherein the cleaning body comprises:
a first part extending horizontally with respect to an upper surface of the mattress;
a second part extending vertically from both sides of the first part for facing side surfaces of the mattress; and
a third part extending from the second part in an inward direction with respect to the second part; and wherein
the transfer motor is installed at the third part.

19. A bed comprising:
a frame;
and the cleaner of claim 1.

* * * * *